United States Patent [19]

Graham

[11] 4,402,396
[45] Sep. 6, 1983

[54] INTRAOCULAR LENS CASE

[75] Inventor: William M. Graham, Burton, Wash.

[73] Assignee: Cooper Laboratories, Inc., Palo Alto, Calif.

[21] Appl. No.: 348,684

[22] Filed: Feb. 16, 1982

[51] Int. Cl.³ .................. B65D 81/18; B65D 25/54; A61F 1/16; A61F 1/18

[52] U.S. Cl. ................ 206/5.1; 206/45.34; 206/560; 356/246

[58] Field of Search ............ 206/5.1, 45.34, 0.82, 206/357, 210, 557, 560; 356/246

[56] References Cited

U.S. PATENT DOCUMENTS

| | | | |
|---|---|---|---|
| 2,388,221 | 10/1945 | Smith | 206/0.82 |
| 3,373,862 | 3/1968 | Minchin | 206/357 |
| 3,394,717 | 7/1968 | Hollinger | 206/5.1 |
| 4,113,088 | 9/1978 | Binkhorst | 206/45.34 |
| 4,173,281 | 11/1979 | Trought | 206/5.1 |
| 4,269,307 | 5/1981 | LaHaye | 206/45.34 |
| 4,320,831 | 3/1982 | Szabo et al. | 206/0.82 |

*Primary Examiner*—William T. Dixson, Jr.
*Attorney, Agent, or Firm*—Christensen, O'Connor, Johnson & Kindness

[57] ABSTRACT

A lens case for an intraocular lens includes a base carrying a receptacle for a lens holder and a soaking tray. The lens holder is positioned in the receptacle for sliding movement between a first position wherein the lens is securely and protectively held in the lens holder and a second position wherein the lens is released from the lens holder ready for removal from the case.

8 Claims, 6 Drawing Figures

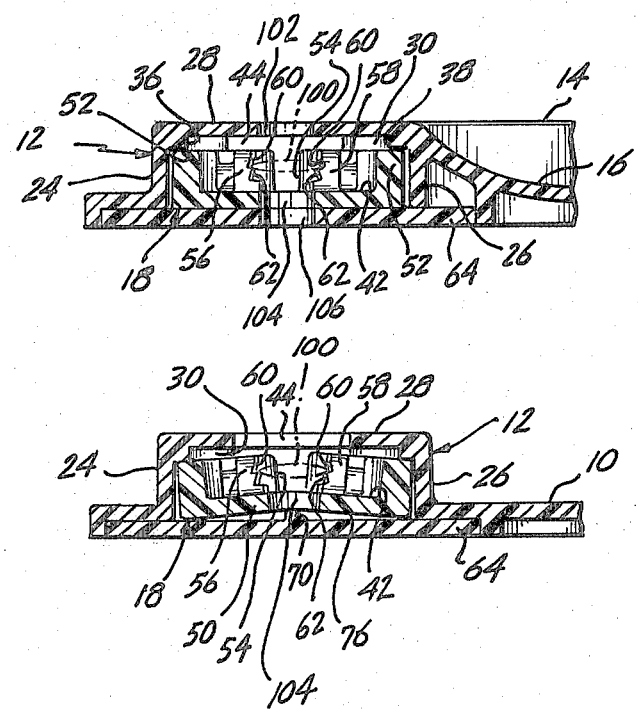

INTRAOCULAR LENS CASE

BACKGROUND OF THE INVENTION

The present invention relates to apparatus for safely transporting an implantable intraocular lens from the manufacturing facility to the implanting physician, and more particular to an intraocular lens case that minimizes the handling of the intraocular lens between the time it is initially manufactured and the time it is prepared for the implanting procedure.

Intraocular lenses are manufactured in a variety of configurations. All, however, include an optical portion (optic) carrying two or more positioning loops (haptics) that extend outwardly from the optic. These loops are generally composed of monofilament polymeric materials that are adhesively or otherwise affixed to the optics.

Currently, once a lens is manufactured, it is placed in a case in which it resides during quality control, measurement, and sterilization procedures prior to shipment to a customer. The lens usually remains in the case between the time it is shipped and the time it is removed from the case in preparation for the implanting procedure.

In the past, intraocular lenses have been placed in conventional contact lens cases for handling and shipment. Merely placing them in a contact lens case has allowed the lenses to be dropped, lost or damaged in handling. As a consequence, the lenses of at least one manufacturer have been placed in a holder that comprises a small cup-like member. The cup-like member has a flat bottom surface with a zone of weakness running diametrically across its bottom surface. A pair of posts extend upwardly on each side of the zone of weakness. The posts each carry two sets of opposing detents that are separated by 6.0 mm and 5.0 mm respectively. Intraocular lenses depending on size are placed in one of the sets of detents by flexing the cup-like member along its zone of weakness, thus causing the posts to be spread apart. The lens can then be dropped into place while the cup-like member is allowed to flex back to its original position to securely hold the intraocular lens in the lens receiving detents. This cup-like holder is normally positioned in an ordinary contact lens case during the manufacturing procedures and subsequent shipping.

This cup-like holder does eliminate the need to directly handle the lens except for a final inspection and in preparation for implanting the lens. Once the lens is positioned in the holder, however, the holder must be inserted in and removed from the contact lens case several times prior to shipment. For example, it must be removed from the contact lens case in order to inspect the lens for loop tip-to-loop tip dimensional tolerance, which is usually done with the aid of an optical comparator. Once the dimensional tolerance is checked, the holder and associated lens can again be placed in the contact case and the lid closed. The lens case is then moved to a next quality control station where a power reading is taken. In order to take the power reading, the lens holder must be removed from the case, measured and returned to the case. Lastly, at a final inspection, the lens and holder are again removed from the contact lens case, the holder flexed to remove the lens so that it can be visually inspected. Once the visual inspection is complete, the cup-like holder is again flexed, the lens inserted and the lens and holder returned to the contact lens case. Thereafter, the case holder and lens are placed in a sterilized bag and are subjected to a sterilization procedure after which they are prepared for shipment.

To prepare the lens for use, the lens case is first removed from the sterilized bag and the lens holder is removed from the lens case. This procedure is done either by a physician or an operating room technician. If the physician or technician is not familiar with the use and operation of the lens holder, removal of the lens from the lens holder is sometimes attempted by grasping a loop with a forceps and attempting to pull the lens from the case, more likely than not separating the loop from the optic, but not removing the lens from the holder. As a consequence, the lens is rendered unusable.

It is therefore desirable to place the lenses in a case that eliminates much of the lens case and holder manipulation during manufacture as well as eliminates the possibility of damage to a lens upon removal from the case.

SUMMARY OF THE INVENTION

The present invention provides an improved lens case that reduces handling of the lens and lens holder as well as eliminates the possibility of damage to the lens upon removal from the holder. The present invention includes a lens holder having a base portion and a flexure zone extending across the base portion. The case includes a pair of lens holding members located on opposite sides of the flexure zone. The lens holding members have opposing lens receiving surfaces. The holder is flexible along the flexure zone between a first position wherein the lens receiving surfaces are spaced from each other by a predetermined distance substantially equal to the diameter of a lens to be held by the members and a second position wherein the members are moved away from each other so that the lens receiving surfaces are spaced from each other by a distance greater than the diameter of the lens. The lens case further includes a receptacle means for receiving the lens holder and an actuating means associated with receptacle means for flexing the lens holder between the first and second positions.

In a preferred form, the flexure zone extends in a substantially straight line across the base portion. The actuating means includes a ramp positioned within and operatively associated with the receptacle means. The ramp and the lens holder are movable relative to each other between a rest position wherein the ramp and lens holder are spaced from each other and an actuated position wherein the ramp is positioned under the zone of flexure. The lens holder is restrained in the receptacle means so that when the lens holder and the ramp are in the actuated position, the lens holder is flexed to its second position, thus releasing any lens that is held by the lens holding members. Preferably, case material is transparent so that overall dimensional measurements and optical power readings can be taken through the case without removing the holder from the receptacle means.

BRIEF DESCRIPTION OF THE DRAWINGS

A better understanding of the present invention can be derived by reading the ensuing specification in conjunction with the accompanying drawings wherein:

FIG. 3 is a longitudinal sectional view of the lens holder and receptacle taken along section line 3—3 of FIG. 1 showing the lens holder in the closed position;

FIG. 4 is a longitudinal sectional view similar to FIG. 3 showing the lens holder in an open position;

FIG. 5 is a full cross sectional view taken along a section line similar to line 5—5 of FIG. 3; and FIG. 6 is a full cross sectional view taken along a section line similar to line 6—6 of FIG. 4.

DETAILED DESCRIPTION OF THE INVENTION

Figure 1:
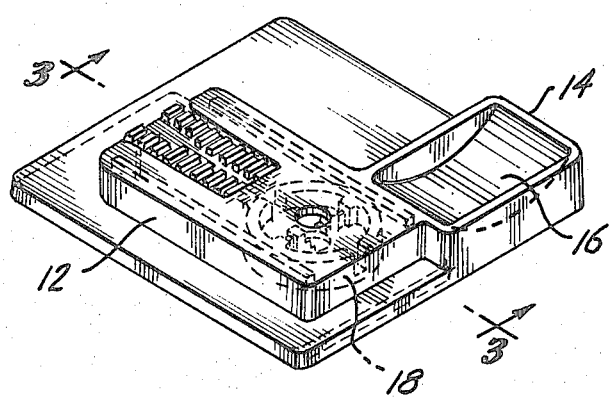
FIG. 1 is an isometric view of a lens assembled in accordance with the present invention.

Referring first to FIG. 1, the lens constructed in accordance with the present invention includes a rectangular base 10, having a generally flat upper surface. A receptacle 12 and a soaking tray 14 that extend upwardly from the surface of the base, and a lens carrier 18 that is slidably received in a chamber defined by the receptacle walls. The receptacle 12 is generally shaped as a right rectangular polyhedron having its longitudinal dimension running in the direction of the longitudinal dimension of the base. The lateral dimension of the receptacle is less than about half of the lateral dimension of the base 10. An upwardly opening soaking tray 14 extends laterally away from one end of the receptacle 12 and is positioned at one corner of the base 10. The tray 14 has a generally concave bottom 16 in which an intraocular lens can be positioned and a saline solution added to prepare the lens for implanting in a patient. The tray occupies only about one sixth of the surface of the base 10 leaving the remaining portion of the base adjacent the tray exposed. This exposed surface is normally used for the application of indicia to identify the style, power, serial number and other identifying information specific to the lens held in the case. Generally, the identifying indicia are placed on an adhesively back label which in turn applied to the exposed portion of the base 10.

Figure 2:
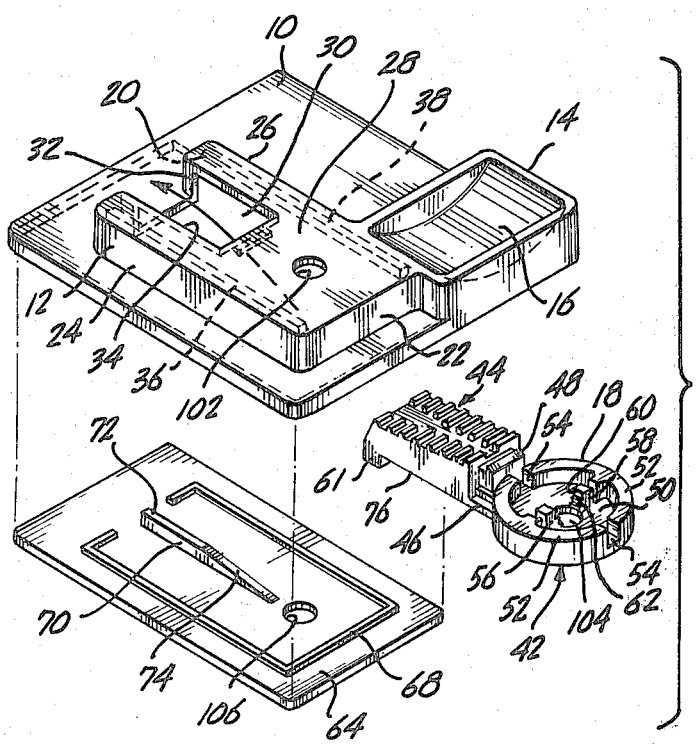
FIG. 2 is an exploded isometric view of a lens case of the present invention.

Referring now conjunctively to FIGS. 1 and 2, the receptacle has end walls 20 and 22, sidewalls 26 and a top wall 28 that generally define a cavity or chamber 30 that extends upwardly from the base 10 and opens downwardly onto the bottom surface of the base 10. The length of the chamber is approximately twice its width. One end wall 20 of the receptacle 12 has a rectangular opening 32 that extends the full heighth of the end wall and is centered in the end wall 30. The width of the opening 32 is approximately half the width of the receptacle 12. A second rectangular opening 34 extends from the upper end of the first end wall opening 32 longitudinally across the top wall 28 of the receptacle and terminates at about the center portion of the receptacle 12. The width of the opening 34 is equivalent to that of the end wall opening 32. A pair of rails 36 and 38 are positioned inside the chamber 30. The rails 36 and 38 are positioned adjacent the sidewalls 24 and 26 and extend the full length of the receptacle 24. The bottom edges of the rails are spaced downwardly from the bottom surface of the top wall 28. The purpose of these rails will become more apparent when the operation of the lens case is explained in further detail below.

Referring conjunctively to FIGS. 2 and 3, the lens carrier 18 includes a cup-like lens holder 42, a pull tab 44, connecting members 46 and a latch member 48. The lens holder 42 is circular in plan view and includes a bottom wall 50 and upwardly extending circular sidewalls 52. The diameter of the holder is slightly less than the width of the chamber 30 of the receptacle 12. The walls 52 carry diametrically opposed slots 54 that extend from the upper edges of the walls 52 down to the bottom surface 50. These slots 54 create a zone weakness in the holder extending along the diameter on which the slots are located so that the holder can be flexed or bent along the zone of weakness.

A pair of lens holding posts 56 and 58 extend upwardly from the bottom surface of the cup 50. The posts are oriented along a diameter that is orthogonally oriented relative to the diametric zone of weakness. Referring to FIGS. 3 and 5, each of the posts 58 carries opposing lens receiving surfaces 60 and 62. The lens receiving surface 60 are spaced from each other by a distance equal to the diameter of a standard intraocular lens, for example, 5 mm. The other set of lens receiving surfaces 62 are spaced from each other by a distance equivalent to a smaller lens diameter, for example, 3 mm. The operation and function of these lens receiving surfaces will be explained in greater detail below.

The lens holder 42 is coupled to the pull tab 44 by a pair of angle shaped connecting beams 46, one of which can be seen in the FIG. 2, and the other of which can be seen in FIG. 3. The outer edges of these angled shaped connecting members 46 are spaced from each other by a distance substantially equivalent to the width of the pull tab 44. The pull tab 44 is generally rectangularly shaped in plan view and is sized to fit through the opening 30 in the upper surface of the receptacle 12. The pull tab extends the full length of the opening 34 from its inner edge longitudinally beyond the end wall 20. The pull tab has a downwardly extending leg 61, the bottom surface of which slidably engages the upper surface of the base 10 adjacent the opening 32. When the lens carrier 18 is positioned in the chamber 30, and the pull tab 44 is positioned in the opening 34, the cup holder 42 resides under the portion of the top wall 28 that is located between the inner edge of the opening 34 and the end wall 22 opposite the end wall opening 32. The carrier 18 is held in position by a base plate 64. Base plate 64 is rectangularly shaped and has a width and length that is slightly larger than the width and length of the receptacle 12. The base plate 64 fits into a cavity 66 located in the bottom portion of the base 10 under the receptacle. The base plate carries an upwardly extending rectangular ridge 68 that has an external dimension substantially the same as the chamber 30. The rectangular ridge 68 engages the bottom portions of the end sidewalls to position the base plate under the receptacle 30.

The base plate 64 also carries a ramp 70. When the base plate is in position, the ramp 70 extends upwardly into chamber 30 below the top wall opening 34. The ramp has a raised surface 72 that is parallel to the upper surface of the base plate 70. The raised surface 72 extends longitudinally from the central portion of the end wall opening 32 toward the opposite end wall 22. The length of the raised surface 72 however is slightly less than that of the opening 34 and the upper wall 28. The ramp also has an inclined surface 74 that extends from the inner end of the raised surface 72 downwardly toward the upper surface of the base plate 64. The inclined surface 74 terminates at a location between the inner end of the opening 34 and the end wall 22.

The base, receptacle and soaking tray are preferably all integrally formed or molded from a transparent polymeric material such as butyrate. The base plate is formed from a similar material. The base and base plate are thus relatively rigid and impact resistant. The lens carrier is integrally formed from a different polymeric material, for example, polyethylene, that in relatively thin cross sections in flexible. Thus, the lens holder 42 can be flexed along the diameter on which the slots 54 lie to spread the lens holding posts as will be understood in greater detail below. Similarly, the inner end of the pull tab 44 can be flexed up and down because of the relatively small cross section of the connecting members 46 to latch and unlatch the holder from its closed position.

Referring now to FIGS. 3, and 5, the lens case is illustrated in its assembled form with the lens carrier 18 in a closed position. The bottom surface 76 of the holder 42 and pull tab 44 is inclined upwardly from a location on the cup holder bottom surface opposite the pull tab to the location of the leg 61 of the pull tab 44. Further, the interior of the pull tab 44 is hollow to form a cavity 78 that not only saves material during molding of the pull tab but also allows the ramp 70 to extend slightly upwardly past the sidewalls of the pull tab 44. In the closed position, the upwardly extending latch member 48 that is located adjacent the inner end of the pull tab 44 is positioned behind a downwardly extending ridge 80, which can also be seen in FIG. 2. The co-action of the latch member 48 and ridge 80 prevents movement of the lens carrier until the latch member 48 is disengaged.

Still referring to FIGS. 3 and 5, a lens 100 is shown positioned between lens receiving surface 60 on the post 58. In this position, the lens holder 42 is in its relaxed position and is not flexed along its zone of weakness. Thus, the lens 100 is held securely in the lens receiving surface 60. When the lens carrier is in its closed position, it is not necessary to remove the lens once it is initially placed in the holder until it is ready for use by a physician. Because the receptacle material is transparent, the necessary visual inspections and loop measurements can be made while the lens is in the holder. Additionally, a plurality of vertically aligned openings 102, 104 and 106 that are respectively located in the upper wall 28 of the receptacle, the bottom wall 50 of the lens holder 42 and the base plate 64 are provided so that sterilization gas can be readily circulated through the lens case and past the lens. In addition, these axially aligned holes allow for optical measurements to be made while the lens is positioned in the case.

To remove the lens 100 from the case, the thumb or forefinger is placed on the upper surface of pull tab 44 and the pull tab is pressed down to release the latch 48 from the latch ridge 80. The pull tab is then moved longitudinally outwardly from the receptacle, thus moving the lens holder 42 from its closed position adjacent end wall 22 to an open position adjacent end wall 20, as shown in FIGS. 4 and 6. In this position, the lens 100 is positioned below the opening 34 and the upper wall 28 of the receptacle. The lens 100 is released from the lens receiving surfaces 60 of the posts 58 by the co-action of the ramp 70 with the lens holder 42 along its zone of weakness. As the cup holder is moved to its closed position adjacent wall 20, the bottom surface of the cup holder 42 rides up on the inclined portion 74 of the ramp 70. The zone of weakness in the holder 42 is oriented relative to the ramp 70 so that the ramp engages the zone of weakness along the bottom surface of the holder 42, thus causing the bottom surface to be raised along its zone of weakness relative to the upper surface of the base plate 64. At the same time the upper edges of the sidewalls 52 at locations along the diameter of the cup holder 42 oriented orthogonally from the zone of weakness engage the rails 36 and 38 in the chamber 30 so that the elevation of the sidewalls relative to the upper surface of the base plate 64 is not changed as the cup holder is moved toward its open position. Thus, the cup holder is flexed along its zone of weakness, this flexure causes the lens holding post 58 to be moved away from each other, automatically causing the lens receiving surfaces to disengage from the periphery of the lens, freeing the lens, and allowing it to be extracted from the lens holder without damage.

Of course, a lens is initially positioned in the case after its manufacture, by pulling the lens holder to its open position as shown in FIGS. 4 and 6, dropping the lens into position between the cup holding posts and then pushing the pull tab into its closed position in opening 34 to reposition the cup holder adjacent end wall 22 of the receptacle. At the same time, the latch member 48 engages the latch ridge 80 to secure the lens carrier in its closed position.

The present invention has been disclosed in relation to a preferred embodiment. One of ordinary skill after reading the foregoing specification will be able to make various changes, substitutions of equivalents and other alterations without departing from the broad concepts disclosed herein. For example, one of ordinary skill will readily see that an alternative means for flexing the cup holder between the open and close position is to provide for a movable ramp and stationary cup holder, because relative movement of the two is all that is required to flex the lens holder. It is therefore intended that the Letters Patent granted hereon be limited only by the definitions contained in the appended claims and equivalents thereof.

The embodiments of the invention in which an exclusive property or privilege is claimed are defined as follows:

1. A lens case comprising:
   a lens holder having a base portion and a flexure zone extending across said base portion, said case including a pair of lens holding members located on opposite sides of said flexure zone, said lens holding members having opposing lens receiving surfaces, said holder being flexible along said flexure zone between a first position wherein said lens receiving surfaces are spaced from each other by a predetermined distance substantially equal to the diameter of a lens to be held by said members and a second position wherein said members are moved away from each other so that said lens receiving surfaces are spaced from each other by a distance greater than the diameter of a lens,
   receptacle means for receiving said lens holder, and
   actuating means associated with said receptacle means for flexing said lens holder between said first and second positions.

2. The lens of claim 1 wherein said flexure zone extends in a substantially straight line across said base portion, said actuating means including a ramp positioned within and operatively associated with said receptacle means, said ramp and said lens holder being moveable relative to each other between a rest position wherein said ramp and said lens holder are spaced from each other and an actuated position wherein said ramp is positioned under said zone of flexure, said lens holder being restrained by said receptacle means so that when said lens holder and said ramp are in said actuated position, said lens holder is flexed to said second position.

3. The lens of claim 2 wherein said receptacle means comprises an elongated chamber having a first end, a second end, top wall and bottom wall, said lens holder being mounted in the said chamber for reciprocating movement between said first and second ends of said chamber, said top wall having an opening therein located adjacent said second end, said ramp being positioned on and protruding upwardly from said bottom wall adjacent said second end, said ramp being inclined downwardly toward said bottom wall as said ramp extends towards said first end.

4. The lens case of claim 3 further comprising:
tab means affixed to said lens holder and extending out of said opening when said lens holder is positioned adjacent said first end.

5. The lens case of claim 4 further comprising:
latch means associated with said tab means and said receptacle means for releasably locking said lens holder adjacent said first end.

6. The lens case of claim 5 further comprising:
a base member, said receptacle means being mounted on said base member, said base member having a surface for receiving instruction indicia.

7. The lens case of claim 6 wherein said base member further includes a soaking tray located adjacent said receptacle means.

8. The lens case of claim 3 wherein said lens holder has upwardly extending side portions spaced outwardly from said lens holding members, said side portions having upper edges located above said lens receiving surfaces, said top wall of said receptacle means having rails adjacent each side thereof, the upper edges of said side portions slidably engaging said rails as said lens holder is moved between said first and second ends of said receptacle means, said rails preventing upward movement of the side portions of said lens holder when said holder is moved to the actuated position.

* * * * *